United States Patent
Deshpande et al.

(10) Patent No.: US 6,803,461 B2
(45) Date of Patent: Oct. 12, 2004

(54) SYNTHESIS OF CEFTIOFUR INTERMEDIATE

(75) Inventors: Pramod Narayan Deshpande, Chennai (IN); Bhausaheb Pandharinath Khadangale, Chennai (IN); Surulichamy Senthil Kumar, Chengalpattu (IN); Gautam Kumar Das, Chennai (IN)

(73) Assignee: Orchid Chemicals and Pharmaceuticals Limited, Chennai (IN)

( * ) Notice: Subject to any disclaimer, the term of this patent is extended or adjusted under 35 U.S.C. 154(b) by 0 days.

(21) Appl. No.: 10/208,879

(22) Filed: Aug. 1, 2002

(65) Prior Publication Data

US 2003/0130502 A1 Jul. 10, 2003

Related U.S. Application Data

(63) Continuation-in-part of application No. 10/035,178, filed on Jan. 4, 2002.

(51) Int. Cl.$^7$ .............................................. C07D 501/36
(52) U.S. Cl. ..................................................... 540/226
(58) Field of Search ......................................... 540/226

(56) References Cited

U.S. PATENT DOCUMENTS

| | | |
|---|---|---|
| 4,115,645 A | 9/1978 | Jackson et al. |
| 4,144,391 A | 3/1979 | Hatfield |
| 4,317,907 A | 3/1982 | Saikawa et al. |
| 4,385,178 A | 5/1983 | Saikawa et al. |
| 4,463,173 A | 7/1984 | Jung |
| 4,464,367 A | 8/1984 | Labeeuw et al. |
| 4,472,574 A | 9/1984 | Hug |
| 4,937,330 A | 6/1990 | Sacks et al. |
| 5,387,679 A | 2/1995 | Sogli et al. |
| 5,580,978 A | 12/1996 | Prager et al. |
| 5,597,914 A | 1/1997 | Danklmaier |
| 5,700,932 A | 12/1997 | Lee et al. |
| 5,869,649 A | 2/1999 | Khanna et al. |
| 6,214,997 B1 | 4/2001 | Handa et al. |
| 6,235,896 B1 | 5/2001 | Handa et al. |
| 6,384,213 B1 | 5/2002 | Handa et al. |
| 6,458,949 B1 | 10/2002 | Handa et al. |
| 6,476,220 B2 | 11/2002 | Kumar et al. |
| 2002/0065412 A1 | 5/2002 | Kumar |

FOREIGN PATENT DOCUMENTS

| | | |
|---|---|---|
| IN | 177465 | 1/1997 |
| WO | WO 01/08633 A2 | 2/2001 |
| WO | WO 02/06289 A1 | 1/2002 |
| WO | WO 02/094816 A1 | 11/2002 |

OTHER PUBLICATIONS

John M. Essery et al., "3–Acylthiomethyl Cephalosporins", The Journal of Antibodies, vol. 27, No. 8, pp. 573–578, Aug., 1974, Syracuse, New York.

*Primary Examiner*—Mark L. Berch
(74) *Attorney, Agent, or Firm*—Oliff & Berridge, PLC

(57) ABSTRACT

The present invention relates to a process for preparation of 7-amino-3-[2-(furylcarbonyl)thiomethyl]-3-cephem-4-carboxylic acid (I) by the condensation of 7-aminocephalosporanic acid (II) with furyl-2-carbonylthiol (III) in the presence of borontrifluoride or its complex, in an organic solvent or mixture of solvents at 0–50° C.

39 Claims, No Drawings

SYNTHESIS OF CEFTIOFUR INTERMEDIATE

This application is a continuation in part of U.S. application Ser. No. 10/035,178 filed on Jan. 4, 2002.

FIELD OF THE INVENTION

The present invention discloses an improved process for the preparation of 7-amino-3-[2-(furylcarbonyl)thiomethyl]-3-cephem-4-carboxylic acid represented by formula (I)

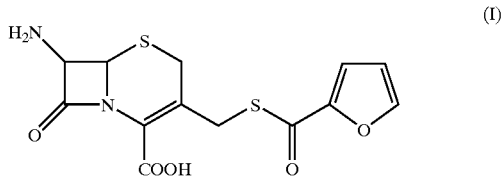

by the condensation of 7-amino cephalosporanic acid (7-ACA) represented by formula (II) with furyl-2-carbonylthiol represented by formula (III) using borontrifluoride or its complex as condensing agent.

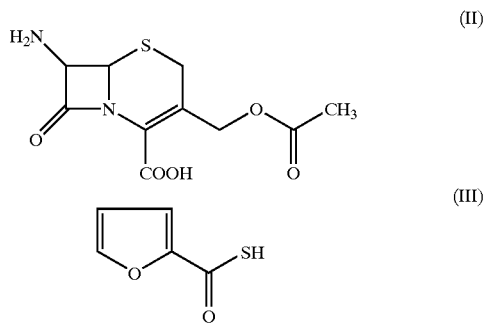

BACKGROUND OF THE INVENTION

Ceftiofur is the generic name given to compound of formula (IV)

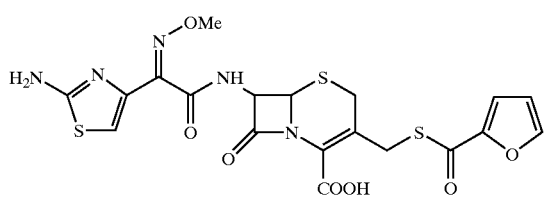

Ceftiofur acid, its alkali metal, alkaline earth metal and amines salts were reported for the first time in U.S. Pat. No. 4,464,367. The ceftiofur is a condensation product of 7-ACA with furyl-2-carbonylthiol and 2-(2-aminothiazol-4-yl)2-methoxyimino)acetic acid at 3 and 7 position respectively. 7-amino-3-[2-(furylcarbonyl)thiomethyl]-3-cephem-4-carboxylic acid represented by formula (I) is the key intermediate which decides the quality and overall yield of the process for making the ceftiofur.

To our surprise there are very few methods reported in the literature for the synthesis of 7-amino-3-[2-(furylcarbonyl) thiomethyl]-3-cephem-4-carboxylic acid of the formula (I). The first report for the synthesis of this intermediate appeared in the U.S. Pat. No. 4,464,367 where the method used for the condensation was taken from a reference from the Journal of Antibiotics 27, 573–8, (1974). These references are about the condensation carried out at a pH of 6.4 using phosphate buffer. The reaction time is very long by following this method and 47% yield is reported for the reaction. These limitations make the process unfavorable for the commercial exploitation.

Another method was disclosed in WO patent 87/01117, which is also merely an extension of the earlier mentioned patent. The condensation was affected by reaction of sodium thiofuroate and 7-ACA at a temperature of 65° C. in aqueous medium at an pH of 6.4. Cephalosporins are known to decompose at high temperature and moreover using the process using this process, the reaction is not completed and yields are also very poor (about 45% and in addition the reaction takes longer time, for example, even after several hours the reaction is incomplete).

Looking at all these problems, a method for the condensation under non-aqueous was reported in U.S. Pat. No. 5,387,679 where condensation of 7-ACA with heterocyclic thiols in the presence of complex of borontrifluoride with dialkyl carbonate was carried out to provide intermediates which are used in the synthesis of cephalosporin antibiotics. When this method was applied for the condensation of 7-ACA and furyl-2-carbonylthiol the reaction mixture was associated with several impurities which could not be separated even during the final purification step. Later on, after several experimentations we found that the stability of furyl-2-carbonylthiol in its solid form is not good, since furyl-2-carbonylthiol belongs to the class of heterocyclic thioacids and not heterocyclic thiol. The behaviour of the reaction is not similar for the thioacids as it was for thiols thereby disallowing the conditions of the U.S. Pat. No. 5,387,679 to be used in the present invention.

In order to overcome the problem, the applicant provides for the first time an improved process for condensing 7-ACA with furyl-2-carbonylthiol which is generated and used in situ in the presence of borontrifluoride in a gaseous state or its solution in an organic solvent to obtain compound of formula (I). This process gives desired compound of formula (I) in excellent yield (90–95%) and high purity 98–99%).

OBJECTS OF THE INVENTION

The primary object of the invention is to provide an improved and commercially viable process for preparing 7-amino-3-[2-(furylcarbonyl)thiomethyl]-3-cephem-4-carboxylic acid of formula (I) as an intermediate for ceftiofur.

Another object of the invention is to use furyl-2-carbonylthiol in situ without isolating it.

Yet another objective of this invention is to provide a process, this will give high yield and excellent purity of the product.

Still another object of the invention is to provide the use of boron trifluoride in gaseous state or its solution in an organic solvent or boron trifluoride complex for carrying out the condensation reaction at low temperature, which is convenient for commercial production.

SUMMARY OF THE INVENTION

Accordingly, the present invention provides the process for preparation of 7-amino-3-[2-(furylcarbonyl)thiomethyl]-3-cephem-4-carboxylic acid (I) by the condensation of 7-aminocephalosporanic acid (II) with furyl-2-carbonylthiol (III) in the presence of borontrifluoride or its complex, in an organic solvent or mixture of solvents at 0–50° C.

The sequence of the reaction is shown below:

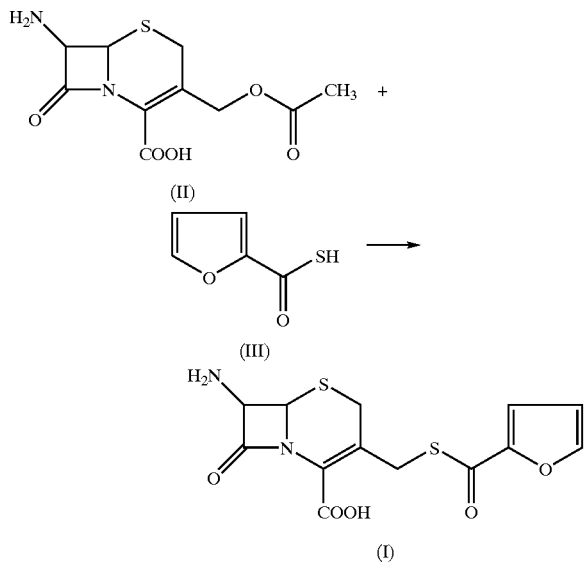

DETAILED DESCRIPTION OF THE INVENTION

In an embodiment the organic solvents used for the condensation is selected from tetrahydrofuran, methyl acetate, ethylacetate, n-propylacetate, iso-propylacetate, n-butylacetate, dichloromethane, toluene, diethylether, di-isopropylether, acetonitrile, acetic acid or mixtures thereof.

In still another embodiment, the boron trifluoride is used in gaseous state, as well as its complex with diethyl ether, in solvents such as acetonitrile, ethylacetate and other compatible solvents. Boron trifluoride is used in 4–8 mole equivalents for 1.0 moles of 7-ACA.

In yet another embodiment the reaction is carried out preferably at a temperature in the range of 30–40° C. The reaction is monitored for completion of the reaction by measuring the content of 7-ACA in the reaction mixture. The content of the 7-ACA should be less than 1%. The content of the 7-ACA reaches to less than 1% within 3–5 hours. After completion of reaction, the mass is poured into water and pH is adjusted to 3–4 by addition of a base. The base used is selected from aqueous ammonia, ammonium hydroxide, sodium hydroxide, sodium carbonate, triethylamine, tributylamine. The solid product is filtered and washed with a solvent and water mixture. The solvent used is selected from tetrahydrofuran, methyl acetate, ethylacetate, n-propylacetate, iso-propylacetate, n-butylacetate, dichloromethane, toluene, diethylether, di-isopropylether, acetonitrile, acetic acid or mixtures thereof In yet another embodiment there is provided a process for the preparation of ceftiofur using the 7-amino-3-[2-(furylcarbonyl)thiomethyl]-3-cephem-4-carboxylic acid represented by formula (I) prepared by a process described above by conventional methods.

In still yet another embodiment, furyl-2-carbonylthiol is prepared in situ from furyl-2-carbonyl chloride/sodium sulphide or furyl-2-carbonyl chloride/sodium hydrogen sulphide.

The invention is illustrated with following examples, which are provided by way of illustration only and should not be construed to limit the scope of the invention.

EXAMPLE—I

7-Amino-3-(2-furanylcarbonyl)thiomethyl]-3-cephem-4-carboxylic acid

Sodium sulfide (54.6 g) is charged to water (600 ml) and furyl-2-carbonylchloride (50.0 g) is added in 1.0 hr at temperature of 20° C. Ethyl acetate is added to it and pH of the mass is adjusted to 1.0 using hydrochloric acid. The organic layer is separated, dried over anhydrous sodium sulphate, filtered to yield furyl-2-carbonylthiol in ethylacetate.

In an another flask ethylacetate (350 ml) is charged and boron trifluoride gas (124.0 g) is purged into it. 7-Amino-cephalosporanic acid (91.0 g) is added at 10.0° C. into this solution of borontrifluoride followed by the addition of furyl-2-carbonylthiol solution in ethylacetate (prepared above). The reaction is completed after stirring for 4–5 hr at 30–40° C., after completion of the reaction, the mixture is poured into mixture of ice cold water. The pH of the solution is adjusted to 3.45–3.55 by addition of aqueous ammonia. The solid precipitated is filtered and washed with mixture ethylacetate to get of 7-amino-3-(2-furanylcarbonyl)thiomethyl]-3-cephem-4-carboxylic acid (110.0 g) with 98–99% HPLC purity.

EXAMPLE—II

7-Amino-3-(2-furanylcarbonyl)thiomethyl]-3-cephem-4-carboxylic acid

Sodium sulfide (36.4 g) is charged to water (400 ml) and furyl-2-carbonylchloride (33.3.0 g) is added in 1.0 hr at temperature 20° C. Ethyl acetate is added to it and pH of the mass is adjusted to 1.0 using hydrochloric acid. The organic layer is separated, dried over anhydrous sodium sulphate, filtered to yield furyl-2-carbonylthiol in ethylacetate.

In an another flask containing acetonitrile (350 ml), boron trifluoride gas (85.0 g) is purged into it. 7-Amino-cephalosporanic acid (60.6 g) is added at 10.0° C. into this solution of borontrifluoride followed by the addition of furyl-2-carbonylthiol solution in ethylacetate (prepared above). The reaction is completed after stirring for 4–5 hr at 30–40° C. After completion of the reaction mass, is poured into ice cold water. The pH of the solution is adjusted to 3.45–3.55 by addition of aq. ammonia. The solid precipitated is filtered and washed with mixture of water and acetonitrile to get of 7-amino-3-(2-furanylcarbonyl)thiomethyl]-3-cephem-4-carboxylic acid (69.0 g) with 97–98% HPLC purity.

EXAMPLE—III

7-Amino-3-(2-furanylcarbonyl)thiomethyl]-3-cephem-4-carboxylic acid

Sodium sulfide (54.6 g) is charged to water (600 ml) and furyl-2-carbonylchloride (50.0 g) is added in 1.0 hr at temperature of 20° C. Ethyl acetate is added to it and pH of the mass was adjusted to 1.0 using hydrochloric acid. The organic layer is separated, dried over anhydrous sodium sulphate, filtered to yield furyl-2-carbonylthiol in ethylacetate.

In an another flask containing acetonitrile (350 ml), 7-amino-cephalosporanic acid (91.0 g) is added at room temperature followed by addition of 45–48% boron trifluoride etherate (275.5 ml) at 10.0° C. To this is added furyl-2-carbonylthiol solution in ethylacetate (prepared above). The reaction is completed after stirring for 4–5 hr at 40–50° C. After completion, the reaction mixture is poured into ice cold water. The pH of the solution is adjusted to 3.45–3.55 by addition of sodium carbonate solution. The solid precipitated is filtered and washed with mixture of water and ethylacetate to get 7-amino-3-(2-furanylcarbonylthiomethyl]-3-cephem-4-carboxylic acid (104.0 g) with 97–98% HPLC purity.

EXAMPLE—IV

7-Amino-3-(2-furanylcarbonyl)thiomethyl]-3-cephem-4-carboxylic acid 30.0 g of sodium hydrogen sulfide is dissolved in 350 ml. of water at 18–25° C. 27.5 g of 2-furoyl chloride is added slowly in 40 to 45 mins. at 18–25° C. and stir for 10 mins. at same temperature. Ethylacetate (250 ml) is added and the pH of the reaction mass is maintained below 1.0 with hydrochloric acid. Separate the organic layer and water (175 ml) is added. The pH is adjusted by sodium bicarbonate (19 g) to 7.0 to 7.5. The aqueous layer is separated and ethyl acetate (100 ml) is added. The pH is maintained adjusted to 0.9 to 1.0 with hydrochloric acid and stir for 15 min and separate the organic layer.

In an another flask 200 ml of ethylacetate is charged and cooled to 0 C. 68.5 g boron trifluoride gas is purged into it. EDTA (1.0 g) is added to the reaction mass and the temperature is raised to 15 C and stirred for 10 min. 50.0 g of the 7-Amino-cephalosporanic acid is added at 10° C. into this solution of borontrifluoride followed by the addition of furyl-2-carbonylthiol solution in ethylacetate (prepared earlier). The reaction is completed after stirring for 3–4 hr at 30–40° C. The mixture is then cooled to 15.degree. C. and 285 ml of cold water is added followed by freshly prepared solution of 1 g of sodium metabisulphite in 50 ml water and 0.3 g EDTA disodium in 50 ml water. pH of the solution is adjusted to 3.45–3.55 by addition of aq. ammonia. The solid precipitated is filtered and washed with ethylacetate (50 ml) to get of 7-amino-3-(2-furanylcarbonyl)thiomethyl]-3-cephem-4-carboxylic acid with 98–99% HPLC purity.

We claim:

1. A process for preparation of 7-amino-3-[2-(furylcarbonyl)thiomethyl]-3-cephem-4-carboxylic acid represented by formula (I)

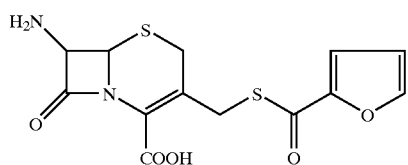
(I)

by the condensation of 7-aminocephalosporanic acid (II)

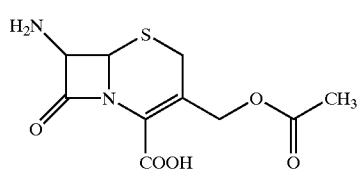
(II)

with furyl-2-carbonylthiol (III)

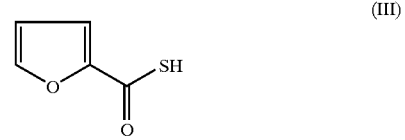
(III)

in the presence of a borontrifluoride complex, in an organic solvent or mixture of solvents at 0–50° C.

2. A process as claimed in claim 1, wherein the organic solvent used for carrying out the condensation reaction is selected from tetrahydrofuran, methyl acetate, ethylacetate, n-propylacetate, iso-propylacetate, n-butylacetate, dichloromethane, toluene, diethylether, di-isopropylether, acetonitrile or mixtures thereof.

3. A process as claimed in claim 1, wherein the borontrifluoride complex is borontrifluoride etherate.

4. A process for the preparation of ceftiofur, comprising:

preparing 7-amino-3-[2-(furylcarbonyl)thiomethyl]-3-cephem-4-carboxylic acid represented by formula (I) by the process of claim 1; and preparing ceftiofur from the 7-amino-3-[2-(furylcarbonyl)thiomethyl]-3-cephem-4-carboxylic acid.

5. A process for the preparation of ceftiofur, comprising:

preparing 7-amino-3-[2-(furylcarbonyl)thiomethyl]-3-cephem-4-carboxylic acid represented by formula (I) by the process of claim 2; and preparing ceftiofur from the 7-amino-3-[2-(furylcarbonyl)thiomethyl]-3-cephem-4-carboxylic acid.

6. A process for the preparation of ceftiofur, comprising:

preparing 7-amino-3-[2-(furylcarbonyl)thiomethyl]-3-cephem-4-carboxylic acid represented by formula (I) by the process of claim 3; and preparing ceftiofur from the 7-amino-3-[2-(furylcarbonyl)thiomethyl]-3-cephem-4-carboxylic acid.

7. A process for preparation of 7-amino-3-[2-(furylcarbonyl)thiomethyl]-3-cephem-4-carboxylic acid represented by formula (I),

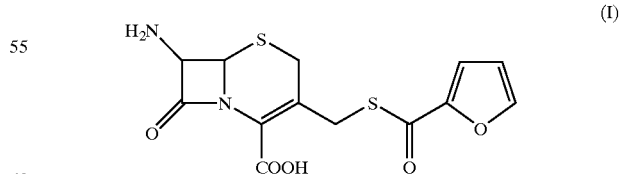
(I)

the said process comprising the step of condensing 7-aminocephalosporanic acid (II) with furyl-2-carbonylthiol (III) in the presence of borontrifluoride or its complex at 20–50° C. in an organic solvent to form a reaction mixture, and isolating the compound of formula (I),

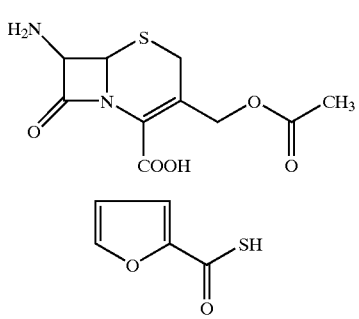

(II)

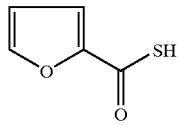

(III)

wherein the reaction mixture of the condensing step is poured into ice cold water, pH of the resulting solution is adjusted to 3–4 with a base to precipitate a solid, the solid is washed with a mixture of water and organic solvent, and the solid is dried at a temperature range of 40°–45° C. under vacuum.

8. A process as claimed in claim 7, wherein the condensing step is performed at a temperature range of 30°–35° C.

9. A process as claimed in claim 3, wherein the pH of the solution is adjusted to 3.45–3.55.

10. A process as claimed in claim 7, wherein furyl-2-carbonylthiol of formula (III) is used in the form of a solution in which said furyl-2-carbonylthiol was prepared, said solution comprising an organic solvent selected from the group consisting of ethylacetate, methyl acetate, propyl acetate, dichloromethane, toluene, diethyl ether, di-isopropyl ether and mixtures thereof.

11. A process as claimed in claim 7, wherein the organic solvent used in the condensing step is selected from the group consisting of ethylacetate, methyl acetate, propyl acetate, dichloromethane, toluene, diethyl ether, di-isopropyl ether, acetonitrile, acetic acid and mixtures thereof.

12. A process as claimed in claim 7, wherein the borontrifluoride is used in a gaseous form or in the form of its solution in an organic solvent selected from ethyl acetate, acetonitrile, methyl acetate, propyl acetate, dichloromethane, toluene, diethyl ether, di-isopropyl ether and mixtures thereof.

13. A process as claimed in claim 7, wherein 3–8 moles of borontrifluoride are used with respect to 7-aminocephalosporanic acid.

14. A process as claimed in claim 7, wherein the base is selected from the group consisting of ammonium hydroxide, sodium hydroxide, and sodium carbonate.

15. A process as claimed in claim 7, wherein the organic solvent used for washing the final product comprises at least one member selected from the group consisting of acetonitrile, ethylacetate, acetone, methyl acetate, propyl acetate, dichloromethane, toluene, diethyl ether, di-isopropyl ether and mixtures thereof.

16. A process as claimed in claim 7, wherein the organic solvent used in the condensing step comprises ethyl acetate.

17. A process as claimed in claim 7, wherein the borontrifluoride is used in a gaseous form.

18. A process as claimed in claim 7, wherein 4.5 moles of borontrifluoride are used with respect to each mole of 7-aminocephalosporanic acid.

19. A process as claimed in claim 7, wherein the base comprises ammonium hydroxide.

20. A process for preparation of 7-amino-3-[2-(furylcarbonyl)thiomethyl]-3-cephem-4-carboxylic acid represented by formula (I),

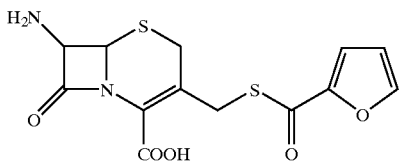

(I)

the said process comprising the step of condensing 7-aminocephalosporanic acid (II) with furyl-2-carbonylthiol (III) in the presence of borontrifluoride in a gaseous form, or its complex, at 20–50° C. in an organic solvent to form a reaction mixture, and isolating the compound of formula (I).

(II)

(III)

21. A process as claimed in claim 20, wherein the condensing step is performed at a temperature range of 30°–35° C.

22. A process as claimed in claim 20, wherein the reaction mixture of the condensing step is poured into ice cold water, and the pH of the solution is adjusted to 3–4 with a base to precipitate a solid.

23. A process as claimed in claim 22, wherein the pH of the solution is adjusted to 3.45–3.55.

24. A process as claimed in claim 22, wherein the solid obtained by precipitation is washed with a mixture of water and organic solvent, and the solid is dried at a temperature range of 40°–45° C. under vacuum.

25. A process as claimed in claim 20, wherein furyl-2-carbonylthiol of formula (III) is used in the form of a solution in which said furyl-2-carbonylthiol was prepared, said solution comprising an organic solvent selected from the group consisting of ethylacetate, methyl acetate, propyl acetate, dichloromethane, toluene, diethyl ether, di-isopropyl ether and mixtures thereof.

26. A process as claimed in claim 20, wherein the organic solvent used in the condensing step is selected from the group consisting of ethylacetate, methyl acetate, propyl acetate, dichloromethane, toluene, diethyl ether, di-isopropyl ether, acetonitrile, acetic acid and mixtures thereof.

27. A process as claimed in claim 20, wherein 3–8 moles of borontrifluoride are used with respect to 7-aminocephalosporanic acid.

28. A process as claimed in claim 22, wherein the base is selected from the group consisting of ammonium hydroxide, sodium hydroxide, and sodium carbonate.

29. A process as claimed in claim 24, wherein the organic solvent used for washing the final product comprises at least one member selected from the group consisting of acetonitrile, ethylacetate, acetone, methyl acetate, propyl acetate, dichloromethane, toluene, diethyl ether, di-isopropyl ether and mixtures thereof.

30. A process as claimed in claim 20, wherein the organic solvent used in the condensing step comprises ethyl acetate.

31. A process as claimed in claim 20, wherein 4.5 moles of borontrifluoride are used with respect to each mole of 7-aminocephalosporanic acid.

32. A process as claimed in claim 22, wherein the base comprises ammonium hydroxide.

33. A process for the preparation of ceftiofur, comprising:
preparing 7-amino-3-[2-(furylcarbonyl)thiomethyl]-3-cephem-4-carboxylic acid represented by formula (I) by the process of claim 7; and
preparing ceftiofur from the 7-amino-3-[2-(furylcarbonyl)thiomethyl]-3-cephem-4-carboxylic acid.

34. A process for the preparation of ceftiofur, comprising:
preparing 7-amino-3-[2-(furylcarbonyl)thiomethyl]-3-cephem-4-carboxylic acid represented by formula (I) by the process of claim 20; and
preparing ceftiofur from the 7-amino-3-[2-(furylcarbonyl)thiomethyl]-3-cephem-4-carboxylic acid.

35. A process as claimed in claim 4, wherein the 7-amino-3-[2-(furylcarbonyl)thiomethyl]-3-cephem-4-carboxylic acid is reacted with 2-(2-aminothiazol-4-yl)2-methoxyimino acetic acid to form the ceftiofur.

36. A process as claimed in claim 5, wherein the 7-amino-3-[2-(furylcarbonyl)thiomethyl]-3-cephem-4-carboxylic acid is reacted with 2-(2-aminothiazol-4-yl)2-methoxyimino acetic acid to form the ceftiofur.

37. A process as claimed in claim 6, wherein the 7-amino-3-[2-(furylcarbonyl)thiomethyl]-3-cephem-4-carboxylic acid is reacted with 2-(2-aminothiazol-4-yl)2-methoxyimino acetic acid to form the ceftiofur.

38. A process as claimed in claim 33, wherein the 7-amino-3-[2-(furylcarbonyl)thiomethyl]-3-cephem-4-carboxylic acid is reacted with 2-(2-aminothiazol-4-yl)2-methoxyimino acetic acid to form the ceftiofur.

39. A process as claimed in claim 34, wherein the 7-amino-3-[2-(furylcarbonyl)thiomethyl]-3-cephem-4-carboxylic acid is reacted with 2-(2-aminothiazol-4-yl)2-methoxyimino acetic acid to form the ceftiofur.

* * * * *